(12) United States Patent
Tah et al.

(10) Patent No.: US 8,048,024 B2
(45) Date of Patent: Nov. 1, 2011

(54) STEERING MECHANISM

(75) Inventors: Richard C. Tah, Framingham, MA (US); Isaac Ostrovsky, Wellesley, MA (US); Jozef Slanda, Milford, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 197 days.

(21) Appl. No.: 12/389,697

(22) Filed: Feb. 20, 2009

(65) Prior Publication Data

US 2009/0234280 A1    Sep. 17, 2009

Related U.S. Application Data

(60) Provisional application No. 61/037,131, filed on Mar. 17, 2008.

(51) Int. Cl.
*A61M 31/00* (2006.01)
*A61M 37/00* (2006.01)

(52) U.S. Cl. .................................. 604/95.04

(58) Field of Classification Search ............ 604/95.01, 604/528, 529, 530, 531, 532; 600/139, 141, 600/142, 146, 147, 148, 149
See application file for complete search history.

(56) References Cited

U.S. PATENT DOCUMENTS

| | | | |
|---|---|---|---|
| 4,566,437 A | 1/1986 | Yamaguchi | |
| 4,617,915 A | 10/1986 | Arakawa | |
| 4,998,916 A | 3/1991 | Hammerslag et al. | |
| 5,060,660 A | 10/1991 | Gambale et al. | |
| 5,281,214 A | 1/1994 | Wilkins et al. | |
| 5,325,845 A * | 7/1994 | Adair | 600/114 |
| 5,347,989 A | 9/1994 | Monroe et al. | |
| D351,652 S | 10/1994 | Thompson et al. | |
| 5,352,237 A | 10/1994 | Rodak et al. | |
| 5,413,107 A * | 5/1995 | Oakley et al. | 600/463 |
| 5,611,777 A | 3/1997 | Bowden et al. | |
| 5,656,030 A | 8/1997 | Hunjan et al. | |
| 5,667,476 A | 9/1997 | Frassica et al. | |
| 5,702,349 A | 12/1997 | Morizumi | |
| 5,860,953 A | 1/1999 | Snoke et al. | |
| 5,882,333 A | 3/1999 | Schaer et al. | |

(Continued)

FOREIGN PATENT DOCUMENTS

DE     26 03 370 A1     8/1977

(Continued)

OTHER PUBLICATIONS

International Search Report and Written Opinion for PCT/US09/48792, mailed on Sep. 22, 2009; 15 pages.

(Continued)

*Primary Examiner* — Christopher D Koharski
(74) *Attorney, Agent, or Firm* — Finnegan, Henderson, Farabow, Garrett & Dunner, LLP

(57) ABSTRACT

A hand-holdable steering mechanism is used as part of a medical device such as a catheter or an endoscope to allow movement of a steerable distal portion of the catheter or endoscope. The mechanism can include a housing, a first actuator, and a second actuator. The first actuator is configured to move the steerable portion along a first plane when the first actuator is moved between first and second positions. The second actuator is configured to move the steerable portion along a second plane different than the first plane when the second actuator is moved between first and second positions.

20 Claims, 7 Drawing Sheets

U.S. PATENT DOCUMENTS

| | | | |
|---|---|---|---|
| 5,897,529 | A | 4/1999 | Ponzi |
| 5,906,590 | A | 5/1999 | Hunjan et al. |
| 5,957,865 | A | 9/1999 | Backman et al. |
| 6,007,531 | A | 12/1999 | Snoke et al. |
| 6,027,473 | A | 2/2000 | Ponzi |
| 6,059,739 | A | 5/2000 | Baumann |
| 6,066,125 | A | 5/2000 | Webster, Jr. |
| 6,123,699 | A | 9/2000 | Webster, Jr. |
| 6,171,277 | B1 | 1/2001 | Ponzi |
| 6,183,435 | B1 | 2/2001 | Bumbalough et al. |
| 6,183,463 | B1 | 2/2001 | Webster, Jr. |
| 6,198,974 | B1 | 3/2001 | Webster, Jr. |
| 6,203,507 | B1 | 3/2001 | Wadsworth et al. |
| 6,267,746 | B1 | 7/2001 | Bumbalough |
| 6,468,260 | B1 | 10/2002 | Bumbalough et al. |
| 6,500,167 | B1 | 12/2002 | Webster, Jr. |
| 6,571,131 | B1 | 5/2003 | Nguyen |
| 6,605,086 | B2 | 8/2003 | Hayzelden et al. |
| 6,679,873 | B2 | 1/2004 | Rabiner et al. |
| 6,783,510 | B1 | 8/2004 | Gibson et al. |
| 6,802,835 | B2 | 10/2004 | Rabiner et al. |
| 6,837,867 | B2 | 1/2005 | Kortelling |
| 6,945,956 | B2 | 9/2005 | Waldhauser et al. |
| 6,966,906 | B2 | 11/2005 | Brown |
| 7,037,290 | B2 | 5/2006 | Gardeski et al. |
| 7,060,024 | B2 | 6/2006 | Long et al. |
| 7,060,025 | B2 | 6/2006 | Long et al. |
| 7,115,134 | B2 | 10/2006 | Chambers |
| 7,232,437 | B2 | 6/2007 | Berman et al. |
| 7,238,180 | B2 | 7/2007 | Mester et al. |
| 2004/0059191 | A1 | 3/2004 | Krupa et al. |
| 2004/0193239 | A1 | 9/2004 | Falwell et al. |
| 2005/0080476 | A1 | 4/2005 | Gunderson et al. |
| 2005/0256375 | A1 | 11/2005 | Freed |
| 2005/0277874 | A1 | 12/2005 | Selkee |
| 2005/0277875 | A1 | 12/2005 | Selkee |
| 2005/0288627 | A1 | 12/2005 | Mogul |
| 2006/0142694 | A1 | 6/2006 | Bednarek et al. |
| 2006/0173448 | A1 | 8/2006 | Scheller et al. |
| 2006/0252993 | A1 | 11/2006 | Freed et al. |
| 2007/0156116 | A1 | 7/2007 | Gonzalez |
| 2007/0203474 | A1 | 8/2007 | Ryan et al. |
| 2007/0219529 | A1 | 9/2007 | Abe et al. |
| 2007/0270647 | A1 | 11/2007 | Nahen et al. |
| 2007/0282167 | A1 | 12/2007 | Barenboym et al. |
| 2008/0051802 | A1 | 2/2008 | Schostek et al. |
| 2009/0171275 | A1 | 7/2009 | Ostrovsky et al. |

FOREIGN PATENT DOCUMENTS

| | | | |
|---|---|---|---|
| EP | 0 521 595 | B1 | 5/1999 |
| EP | 0 668 052 | B1 | 1/2003 |
| WO | WO 93/20878 | A | 10/1993 |
| WO | WO 2007/136754 | A2 | 11/2007 |
| WO | WO 2007/136829 | A1 | 11/2007 |

OTHER PUBLICATIONS

International Search Report and Written Opinion for PCT/US07/11912, mailed on Sep. 12, 2008; 8 pages.

International Preliminary Report on Patentability for PCT/US07/11912, mailed in Dec. 4, 2008; 6 pages.

International Search Report and Written Opinion for PCT/US08/86142, mailed on Mar. 11, 2009; 10 pages.

Notification of Transmittal of the International Search Report and the Written Opinion of the International Searching Authority, or the Declaration. Issued in corresponding international application No. PCT/US2009/034831, mailed May 13, 2009.*

International Search Report and Written Option for PCT/US09/049809, mailed Oct. 28, 2009; 10 pages.

* cited by examiner

STEERING MECHANISM

CROSS-REFERENCE TO RELATED CASE

This application claims priority to, and the benefit of Provisional U.S. Patent Application Ser. No. 61/037,131, filed Mar. 17, 2008, the entirety of which is incorporated herein by reference.

TECHNICAL FIELD

The invention generally relates to a mechanism for controlling articulation of a steerable portion of a medical device, and more particularly to a one-handed or one-fingered steering mechanism. The mechanism can control articulation of the steerable portion on at least two planes so that 360 degree articulation of the steerable portion is achievable.

BACKGROUND INFORMATION

Steering mechanisms are used to steer or direct a medical instrument, for example a catheter or endoscope, to a desired position or location in a body of a patient. One known steering mechanism resembles a joystick. The configuration of the joystick usually includes a plate attached to control wires. The plate, however, must be large to accommodate the desired articulations of the steerable medical device. Additionally, the single control element encompassed in the joystick control mechanism makes the introduction of force leverage difficult, especially in a procedure during which an increased leverage is needed for different articulation planes. Further, all control wires are manipulated by the joystick, and therefore movement of the joystick may cause additional, albeit unintended, articulation of the catheter or endoscope.

Another known steering mechanism includes multiple slidable buttons. Each button is connected to a puller wire so that when the button is moved, the puller wire moves the catheter in a single direction associated with the puller wire. Thus, at least four slidable buttons are required to achieve 360 degree articulation of the catheter or endoscope. The sliding motion of the buttons on this steering mechanism makes introduction of force leverage very difficult. Furthermore, the catheter can only be articulated along one plane at a time unless the user moves more than one button at the same time, which requires that the user either use multiple fingers or continuously move his or her hand to manipulate the buttons and operate the device.

SUMMARY OF THE INVENTION

It is an object of the invention to allow steering operation by a single hand or a single finger of a user. A steering mechanism according to the invention can control 360 degree articulation of a steerable portion of a medical device. A steering mechanism of the invention also can introduce force leverage for articulating a steerable device. A steering mechanism of the invention also can articulate a steerable device along one plane without unintentionally articulating the steerable device along a different plane.

In one aspect, the invention relates to a steering mechanism for use as part of a medical device. The steering mechanism can comprise a housing, a first actuator and a second actuator. The housing can include a proximal end portion and a distal end portion. The housing extends along a longitudinal axis and is configured to be coupled to a device including a steerable member. The first actuator is movably coupled to the housing and is adapted to move between a first position and a second position different than the first position. The first actuator can be movable with respect to a first axis that is different than the longitudinal axis defined by the housing. The first actuator can be adapted to move the steerable member of the device along a first plane when the housing is coupled to the device and when the first actuator is moved between its first position and its second position. The second actuator can be coupled to the housing and can be movable between a first position and a second position with respect to a second axis different than the first axis. The second actuator can be adapted to move the steerable member of the device along a second plane different than the first plane when the housing is coupled to the device and when the second actuator is moved between its first position and its second position.

Embodiments according to this aspect of the invention can include various features. For example, the first actuator can be movable with respect to an axis that is orthogonal to the longitudinal axis defined by the housing. The first actuator and the second actuator can be disposed on the proximal end portion of the housing. In another example, the first actuator can be adapted to move the steerable member of the device along a substantially vertical plane and the second actuator can be adapted to move the steerable member of the device along a substantially horizontal plane. At least one of the first and second actuators is independently movable of the other of the first and second actuators.

The first and second actuators can be adapted for at least one of one-handed or one-fingered operation by a user. At least one of the first and second actuators is adapted to introduce force leverage to a portion of the steering mechanism when the at least one of the first actuator and the second actuator is moved by a user. The second actuator can be adapted to directly transfer motion to a wire coupled to the steerable member of the device. The second actuator can be movably coupled to the first actuator.

In another example, the housing of the steering mechanism can further comprise a cam disposed in the housing. The cam can be coupled to the first actuator and movable between a first position and a second position different then the first position. The steering mechanism can also comprise a wire that includes first and second ends. At least a portion of the wire can engage the cam and at least a portion of the wire can be couplable to the steerable member of the device.

In another aspect, the invention generally involves a medical device that includes an elongated member and a steering mechanism. The elongated member includes a proximal end and a distal end and defines a lumen at least partially therethrough. The elongated member can substantially extend along a longitudinal axis. The elongated member can include a steerable portion, and at least a portion of the steerable portion can be movable along a first plane and a second plane different than the first plane such that the steerable portion is movable in substantially any direction 360 degrees around the longitudinal axis. The steering mechanism is couplable to the elongated member and is adapted for one-fingered operation by a user. The steering mechanism is configured to move the steerable portion of the elongated member along the first plane and along the second plane different than the first plane. The steering mechanism comprises a first actuator and a second actuator. The first actuator is movable with respect to a first axis different than the longitudinal axis, and is adapted to move the steerable portion of the elongated member along the first plane. The second actuator is adapted to move the steerable portion of the elongated member along the second plane, and is selectively actuatable substantially simultaneously with the first actuator.

Embodiments according to this other aspect of the invention can include various features. For example, the second actuator can be movably coupled to the first actuator. The steering mechanism can include a housing that defines a proximal end portion and a distal end portion, and the elongated member can be couplable to the distal end portion of the housing.

In another example, the medical device further comprises a vertical plane wire and a horizontal plane wire. At least a portion of the vertical plane wire can be coupled to the first actuator, and at least a portion of the vertical plane wire can be coupled to the steerable portion of the elongated member. At least a portion of the horizontal plane wire can be coupled to the second actuator, and at least a portion of the horizontal plane wire can be coupled to the steerable portion of the elongated member. The housing of the steering mechanism can define an interior cavity, and the vertical and horizontal plane wires can each extend from the steerable portion of the elongated member through at least a portion of the interior cavity of the housing.

In another example, the steering mechanism can further comprise a housing that defines an interior cavity and a cam disposed in the interior cavity. The cam can be coupled to the first actuator and configured to move between a first position and a second position different than the first position in response to movement of the first actuator. The medical device can further include first and second vertical plane wires. The first and second vertical plane wires can be coupled to the steerable portion of the elongated member. At least a portion of each of the first and second vertical plane wires can be coupled to the cam. The first and second vertical plane wires can be movable in response to movement of the first actuator. The first vertical plane wire can be adapted to move the steerable portion of the elongated member in a first direction along the first plane, and the second vertical plane wire can be adapted to move the steerable portion in a second direction along the first plane different than the first direction along the first plane.

In a further example, the medical device can include first and second horizontal plane wires. The first and second horizontal plane wires can be coupled to the steerable portion of the elongated member, and at least a portion of each of the first and second horizontal plane wires can be coupled to the second actuator. The first and second horizontal plane wires can each be movable in response to movement of the second actuator. The first and second horizontal plane wires can be adapted to move the steerable portion of the elongated member in a first direction and a second direction different than the first direction, respectively, along the second plane.

BRIEF DESCRIPTION OF THE DRAWINGS

For a fuller understanding of the nature and operation of various embodiments according to the present invention, reference is made to the following description taken in conjunction with the accompanying drawing figures which are not necessarily to scale and wherein like reference characters denote corresponding or related parts throughout the several views.

DESCRIPTION

Apparatuses for controlled articulation of a steerable device are described herein. For example, in some embodiments, the apparatus is a steering mechanism for use as part of a medical device. The steering mechanism can be used as part of or with a medical device including a steerable member, such as, for example, a catheter or endoscope.

Figure 1:
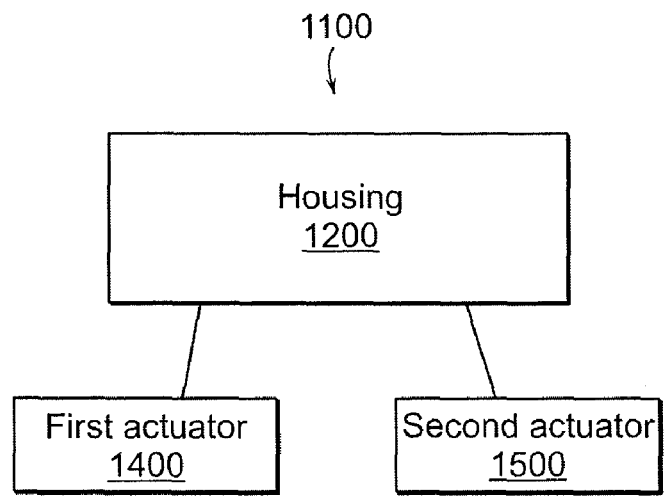
FIG. 1 is a schematic illustration of a steering mechanism for use with or as part of a medical device according to an embodiment of the invention.

In one embodiment, as schematically illustrated in FIG. 1, the apparatus 1100 is a steering mechanism. The steering mechanism 1100 includes a housing 1200, a first actuator 1400, and a second actuator 1500. The housing 1200 is configured to be coupled to a device including a steerable member (not illustrated in FIG. 1).

The first actuator 1400 is coupled to the housing 1200. In some embodiments, the first actuator 1400 is movably coupled to the housing 1200. The first actuator 1400 is configured to move the steerable member of the device. In some embodiments, when the housing 1200 is coupled to the device, the first actuator 1400 is configured to move the steerable member along a first plane when the actuator is actuated.

The second actuator 1500 is coupled to the housing 1200. In some embodiments, the second actuator 1500 is movably coupled to the housing 1200. The second actuator 1500 is configured to move the steerable member of the device. In some embodiments, when the housing is coupled to the device, the second actuator 1500 is configured to move the steerable member along a second plane different than the first plane when the second actuator is actuated.

Figure 2:
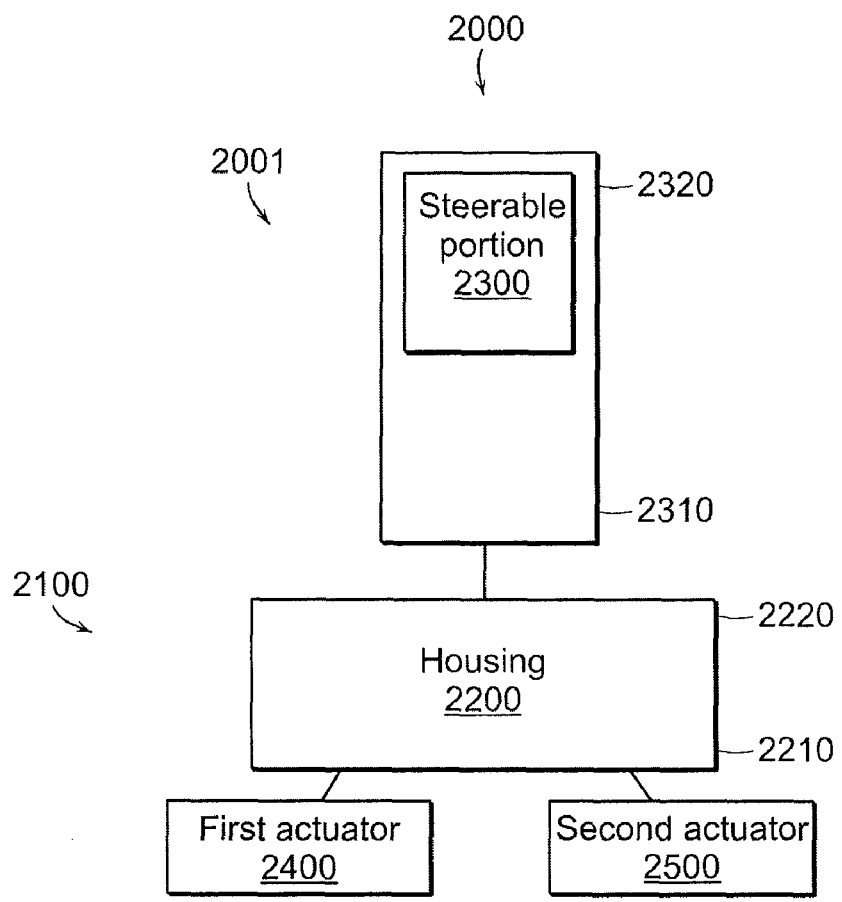
FIG. 2 is a schematic illustration of a medical device according to an embodiment of the invention.

In some embodiments, as schematically illustrated in FIG. 2, the apparatus 2000 is a medical device including an elongated (or steerable) member 2001 and a steering mechanism 2100. The steering mechanism 2100 is configured to control movement (or articulation) of the elongated member 2001.

The elongated member 2001 includes a proximal end 2320 and a distal end 2310 and defines a lumen (not illustrated) therethrough. The terms proximal and distal require a point of reference. In this application, the point of reference is the perspective of the user. Therefore, the term proximal will always refer to an area closest to the user, whereas distal will always refer to an area away from the user. At least a portion of the elongated member 2001 is configured to be steerable. Said another way, in some embodiments, the elongated member 2003 includes a steerable portion 2300. The steerable portion 2300 of the elongated member 2001 is movable along a first plane and a second plane different than the first plane. For example, in some embodiments, the steerable portion 2300 is movable on a vertical plane and a horizontal plane.

The steering mechanism 2100 is couplable to the elongated member 2001. For example, in some embodiments, the steering mechanism 2100 is coupled to the proximal end 2320 of the elongated member 2001.

In some embodiments, the steering mechanism 2100 is adapted for at least one of one-handed or one-fingered operation by a user. Said another way, a user can manipulate or control articulation of the steerable portion of the elongated member by controlling the steering mechanism 2100 with a single hand or finger. The steering mechanism 2100 is configured to move the steerable portion 2300 of the elongated member 2001 along the first plane and the second plane different than the first plane.

In some embodiments, the steering mechanism 2100 includes a first actuator 2400 and a second actuator 2500. The first actuator 2400 is configured to move the steerable portion 2300 of the elongated member 2001 along the first plane. The second actuator 2500 is configured to move the steerable portion 2300 along the second plane.

Figure 3:
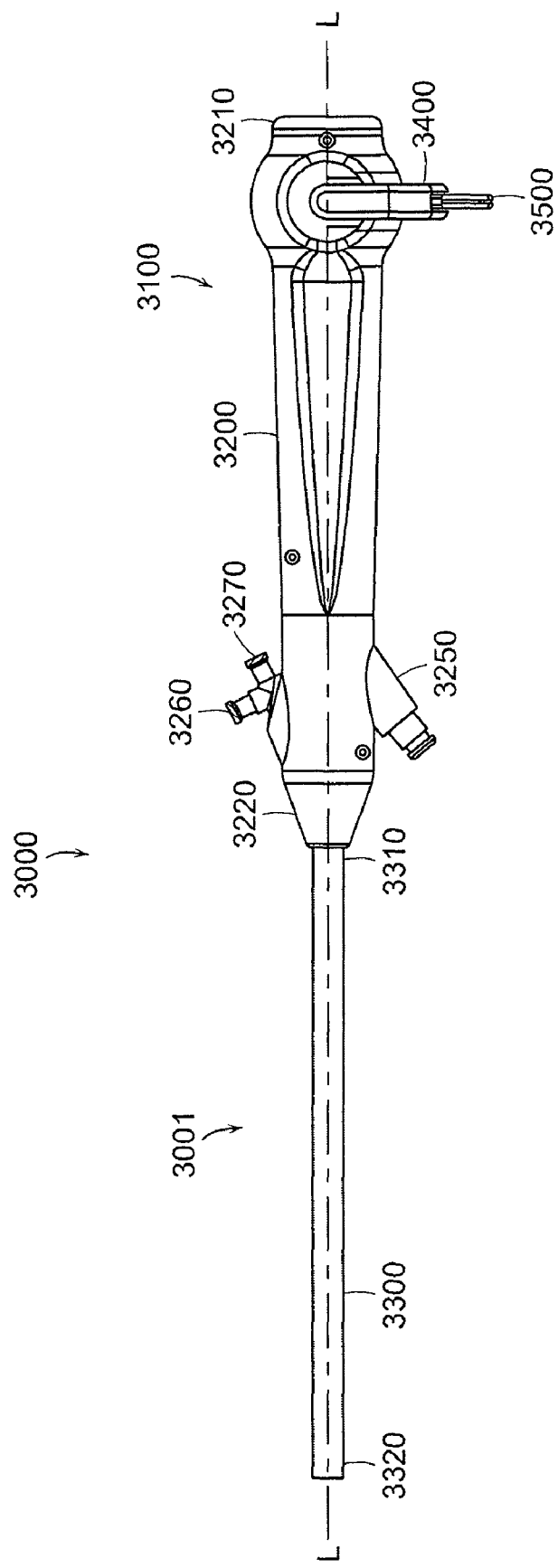
FIG. 3 is a side view of a medical device according to an embodiment of the invention.

As illustrated in FIG. 3, an apparatus 3000, or medical device (also referred to herein as "device"), according to some embodiments of the invention includes an elongated member 3001 and a steering mechanism 3100. The medical device 3000 substantially extends along a longitudinal axis L.

As illustrated in FIG. 3, the elongated member 3001 substantially extends along the longitudinal axis L when the elongated member is in a non-articulated (or relaxed) position (also referred to as the "first position"). In some embodiments, the elongated member 3001 is biased towards the straight or relaxed position. For example, in some embodiments, the elongated member is a catheter or endoscope of greater length (such as compared to the length of the steering mechanism) than the steerable member in the illustrated embodiment.

The elongated member 3001 includes a proximal end 3310 and a distal end 3320 and defines a lumen 3350 at least partially therethrough. At least a portion of the elongated member 3001 is a steerable portion 3300. At least a portion of the steerable portion 3300 is movable along at least a first plane and a second plane different than the first plane. The steerable portion 3300 of the elongated member 3001 is movable in substantially any direction 330 degrees around the longitudinal axis L. In some embodiments, the elongated member 3001 is a catheter or endoscope.

The steering mechanism 3100 is adapted to control articulation of at least a portion of the elongated member 3001 (or steerable member) of the device 3000. In some embodiments, the steering mechanism 3100 is configured to move a steerable portion 3300 of the elongated member 3001 along a first plane and along a second plane different than the first plane.

As illustrated in FIGS. 3-6, in some embodiments, the steering mechanism 3100 includes a housing 3200, a first actuator 3400, and a second actuator 3500. The steering mechanism 3100 is adapted to be coupled to the elongated member 3001. In some embodiments, the steering mechanism 3100 is removably coupled to the elongated member 3001. In the illustrated embodiment, the housing 3200 of the steering mechanism 3100 is couplable to the elongated member 3001. For example, in FIG. 3, a distal end portion 3220 of the housing 3200 is coupled to the elongated member 3001.

Figure 4:
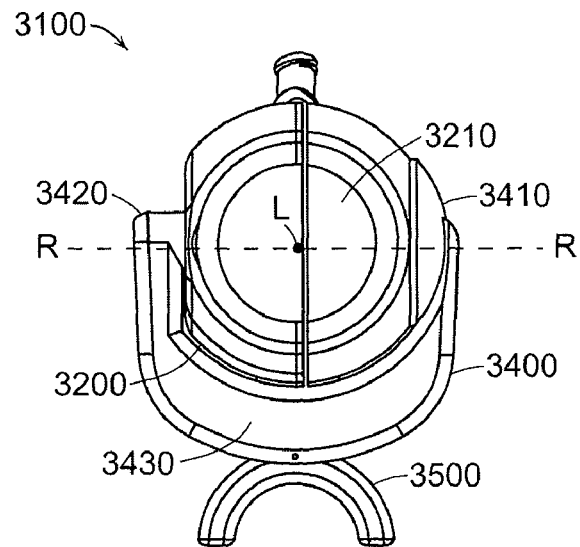
FIG. 4 is an end view of a portion of the medical device of FIG. 3.

As illustrated in FIG. 4, the housing 3200 extends along the longitudinal axis L. The housing 3200 includes a proximal end portion 3210 and a distal end portion 3220. As illustrated in FIG. 6, the housing 3200 defines an interior cavity 3240. In some embodiments, the interior cavity 3240 extends from the proximal end 3210 to the distal end 3220 of the housing 3200.

A cam 3230 is disposed in the housing 3200. The cam 3230 is configured to move the steerable member 3001 of the device 3000. In the illustrated embodiment, the cam 3230 is disposed in the interior cavity 3240 of the housing 3200 towards the proximal end 3210 of the housing. In other embodiments, the cam can be disposed in or on a different portion of the housing.

The cam 3230 is coupled to the first actuator 3400. The cam 3230 is movable between a first position and a second position different than the first position. As described in more detail below, the cam is configured to move in response to movement of the first actuator 3400. Although the steering mechanism 3100 is illustrated and described herein as including a cam 3230 to move the steerable member, in other embodiments, the steering mechanism includes no cam.

Figure 6A:
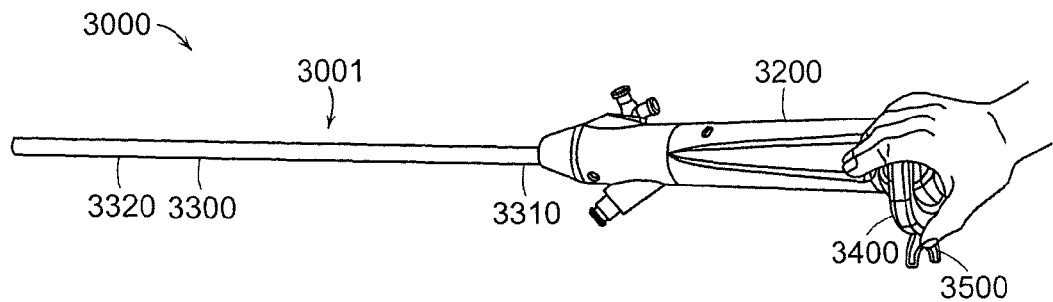
FIGS. 6A-6C are side views of the medical device of FIG. 3 in operation by a user with a first actuator in a first position, second position, and third position, respectively.

The first actuator 3400 of the steering mechanism 3100 is adapted to control articulation of the steerable member 3001 of the device 3000 along at least a first plane. The first actuator 3400 is configured to move the steerable member of the device in at least a first direction and a second direction different than the first direction along the first plane, as illustrated in FIGS. 6A-6C.

Figure 8A:
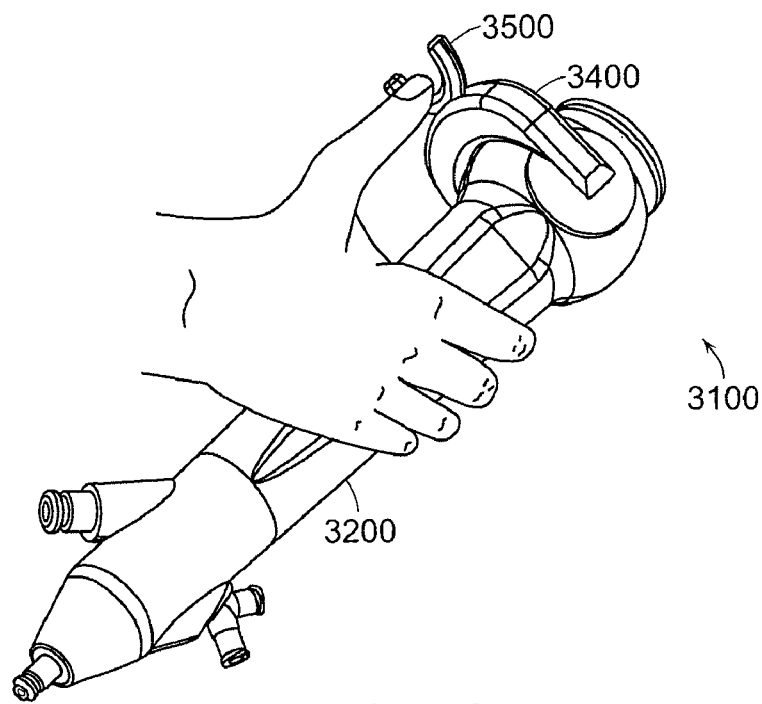
FIGS. 8A and 8B are perspective views of the medical device of FIG. 3 with a user's hand in a first position and a second position, respectively.
Figure 8B:
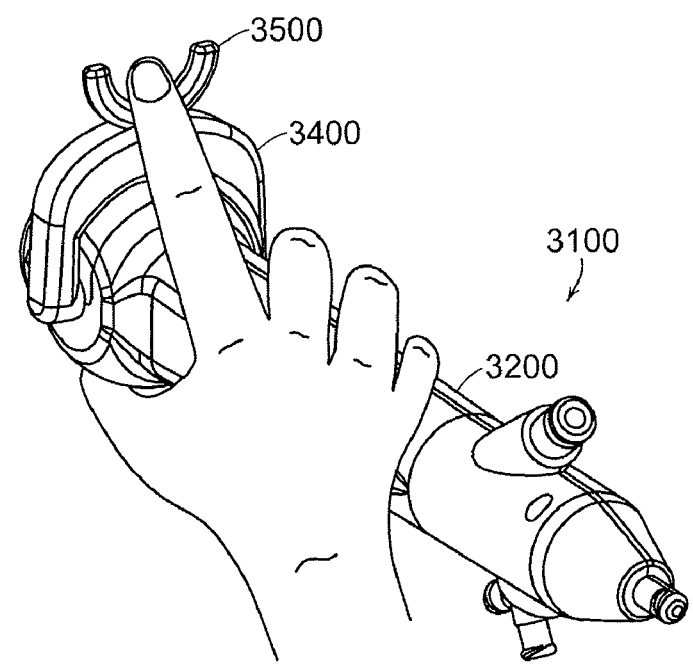

The first actuator 3400 is adapted for at least one of one-handed or one-fingered operation by a user (as illustrated in FIGS. 6A-6C and 8A-8B). For example, during an endoscopic procedure, a physician can hold the housing 3200 of the steering mechanism 3100 in his or her hand while controlling movement of the first actuator 3400 with a thumb of the same hand, as shown in FIG. 8A. In another example, a physician can hold or rest the housing 3200 of the steering mechanism 3100 in his or her hand while controlling movement of the first actuator 3400 with a finger of the same hand, as shown in FIG. 8B.

The first actuator 3400 is movably coupled to the housing 3200. In the illustrated embodiments, the first actuator 3400 is disposed on the proximal end portion 3210 of the housing 3200.

Figure 6B:
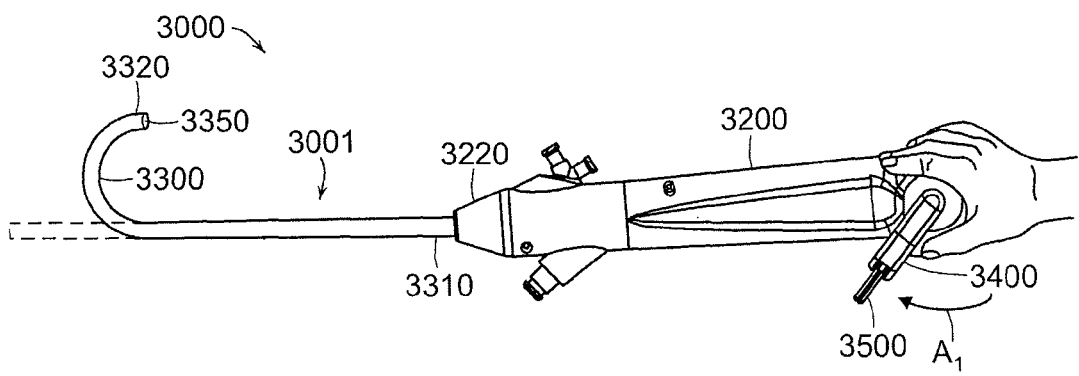
Figure 6C:
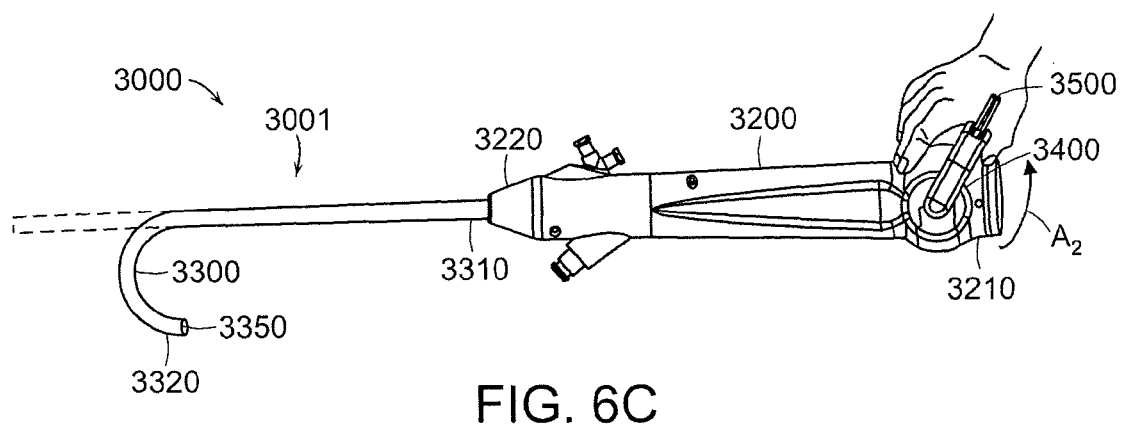

The first actuator 3400 is configured to move between a first (or relaxed) position (illustrated in FIG. 6A) and a second position different than the first position (illustrated in FIG. 6B). When the housing 3200 of the steering mechanism 3100 is coupled to the steerable member 3001 of the device 3000, the first actuator 3400 is configured to move the steerable member along the first plane when the first actuator is moved between its first position and its second position. In some embodiments, the first actuator 3400 is configured to move the steerable member along a substantially vertical plane. In other embodiments, the first actuator is configured to move the steerable member along a different plane.

In some embodiments, the first actuator 3400 is configured to move between its first position and its second position about or with respect to a rotational axis R, illustrated in FIG. 4. The rotational axis R is different than the longitudinal axis L along which the housing extends. In the illustrated embodiment, rotational axis R is orthogonal to the longitudinal axis L defined by the housing.

As illustrated in FIG. 4, in some embodiments, the first actuator 3400 includes a first attachment portion 3410, a second attachment portion 3420, and an arm portion 3430 extending therebetween. At least one of the first attachment portion 3410 and the second attachment portion 3420 is coupled to the housing 3200. The first actuator 3400 turns or pivots at the attachment portions 3410, 3420 coupled to the housing when the first actuator is moved between its first position and its second position. In some embodiments, the arm portion 3430 of the first actuator 3400 is moved, or flipped, about the proximal end 3210 of the housing 3200 when the first actuator 3400 is moved between its first position and its second position. Because the first actuator 3400 pivots at first axis R, for example as opposed to being moved linearly, the first actuator is adapted to introduce force leverage to move the steerable member 3001 of the device 3000.

Although the first actuator 3400 is illustrated and described as including two attachment portions 3410, 3420, in other embodiments, the first actuator can include any number of attachment portions. For example, in one embodiment, the first actuator includes a single attachment portion at which the first actuator is coupled to the housing.

In the illustrated embodiment, the first attachment portion 3410 of the first actuator 3400 is coupled to the cam 3230 disposed within the housing 3200. Movement of the first actuator 3400 between its first position and its second position directly transfers motion onto the cam 3230. Said another way, when the first actuator 3400 is moved from its first position to its second position, the cam 3230 moves from its first position to its second position.

In some embodiments, the steering mechanism 3100 includes a first vertical plane wire 3610 and a second vertical plane wire 3630. The vertical plane wires 3610, 3630 are adapted to move the steerable member 3001 of the device 3000 along the first plane. The first vertical plane wire 3610 is configured to move the steerable member in a first direction along the first plane. In some embodiments, for example, the first vertical plane wire 3610 is configured to move the steerable member in a first vertical direction; for example, "up" from the perspective of the user. All relative descriptions herein such as top, bottom, left, right, up, and down are with reference to the figures, and thus should not be construed in a limiting sense.

The second vertical plane wire 3630 is configured to move the steerable member 3001 of the device 3000 in a second direction different than the first direction along the first plane. In some embodiments, for example, the second vertical plane wire 3630 is configured to move the steerable member 3001 in a second vertical direction different than the first vertical direction; for example, "down" from the perspective of the user.

In some embodiments, the first vertical plane wire 3610 is coupled to the first actuator 3400. For example, the first vertical plane wire 3610 includes a first end and a second end (not shown). In some embodiments, the first end of the first vertical plane wire 3610 is coupled to the first actuator 3400. In the illustrated embodiment, at least a portion of the first vertical plane wire 3610 is engaged with or coupled to the cam 3230, which is coupled to the first actuator 3400.

The first vertical plane wire 3610 is couplable to the steerable member 3001 of the device 3000. For example, in the illustrated embodiment, the second end of the first vertical plane wire 3610 is couplable to the steerable member 3001 of the device 3000.

In some embodiments, the second vertical plane wire 3630 is coupled to the first actuator 3400. For example, the second vertical plane wire 3630 includes a first end and a second end (not shown). In some embodiments, the first end of the second vertical plane wire 3630 is coupled to the first actuator 3400. In the illustrated embodiment, at least a portion of the second vertical plane wire 3630 is engaged with or coupled to the cam 3230, which is coupled to the first actuator 3400.

Figure 5:
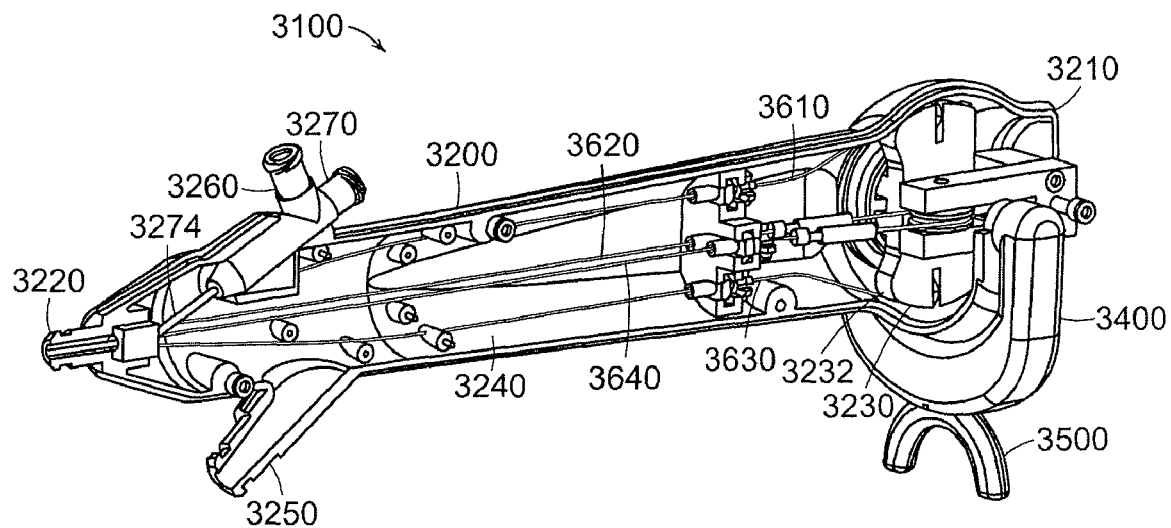
FIG. 5 is a perspective view of a portion of the medical device of FIG. 3 with a portion of a housing removed.

As illustrated in FIG. 5, in some embodiments, the cam 3230 defines at least one groove 3232. The groove 3232 is configured to receive a portion of at least one of the vertical plane wires 3610, 3630. In the illustrated embodiment, the groove 3232 is receiving a portion of the second vertical plane wire 3630.

Although the cam 3230 is illustrated and described as defining a groove 3232, in other embodiments, the cam is otherwise configured to engage the first or second vertical plane wires 3610, 3630. For example, in some embodiments, the cam defines an opening configured to receive a portion of the first or second vertical plane wires 3610, 3630.

The second vertical plane wire 3630 is couplable to the steerable member 3001 of the device 3000. For example, in the illustrated embodiment, the second end of the second vertical plane wire 3630 is couplable to the steerable member 3001 of the device 3000.

The first vertical plane wire 3610 and the second vertical plane wire 3630 are each movable in response to movement of the first actuator 3400. For example, as illustrated in FIG. 6B, movement of the first actuator 3400 in a first direction (indicated by arrow $A_1$) causes movement of the steerable member 3001 in a first direction along the first plane.

When the first actuator 3400 is moved in the first direction from its first position to its second position, the cam 3230 correspondingly moves in a first direction from its first position to its second position. When the cam 3230 moves from its first position to its second position, the vertical plane wire 3610 engaged with or coupled to the cam 3230 correspondingly moves in a first direction from a first position to a second position different than the first position. When the steering mechanism 3100 is coupled to the medical device 3000, movement of the first vertical plane wire 3610 from its first position to its second position moves the steerable member 3001 of the device 3000 in a first direction along a first plane, as illustrated in FIG. 6B.

As illustrated in FIG. 6C, movement of the first actuator 3400 in a second direction (indicated by arrow $A_2$) causes movement of the steerable member 3001 in a second direction along the first plane.

When the first actuator 3400 is moved (or returned) to or towards its first position from its second position, the cam 3230 moves in a second direction different that its first direction to or towards its first position. As the cam moves (or returns) to its first position, the cam moves (or pulls on) the second vertical plane wire 3630, which moves the steerable member 3001 in its second direction along the first plane.

The first actuator 3400 is movable to a third position (illustrated in FIG. 6C) different than its first position and its second position. The first actuator 3400 is movable in the second direction different than the first direction. For example, in some embodiments, the first actuator 3400 is movable in a second direction that is opposite the first direction. The first actuator 3400 is moved in the second direction to its third position from its first or second position.

In FIGS. 6B and 6C, the steerable member 3001 is illustrated in an articulated position, with the non-articulated (or relaxed) position of the steerable member illustrated in broken lines. For example, in some embodiments, the steerable member is a catheter or endoscope of greater length (such as compared to the length of the steering mechanism) than the steerable member in the illustrated embodiments.

Movement of the first actuator 3400 in the second direction to or towards its third position moves the cam 3230 in its second direction different than its first direction to a third position. Movement of the cam 3230 to its third position moves (or pulls on) the second vertical plane wire 3630 in a first direction. Movement of the second vertical plane wire 3630 in its first direction moves the steerable member of the device in its second direction along the first plane, as illustrated in FIG. 6C.

Thus, the steering mechanism 3100 controls articulation of the steerable member of the device along the first plane. The first actuator 3400, in the illustrated embodiment, is configured to control at least bi-directional movement or articulation of the steerable member along the first plane.

As illustrated in FIGS. 3-7, the steering mechanism 3100 of the medical device 3000 includes a second actuator 3500. The second actuator 3500 is configured to move the steerable member of the device along a second plane different than the first plane (along which the first actuator 3400 moves the steerable member). In some embodiments, the second actuator 3500 is adapted to move the steerable member along a second plane that is orthogonal to the first plane. For example, in some embodiments, the second actuator 3500 is adapted to move the steerable member of the device along a substantially horizontal plane.

The second actuator 3500 is coupled to the housing 3200. In the illustrated embodiment, the second actuator 3500 is disposed on or coupled to the proximal end portion 3210 of the housing 3200. Specifically, in the illustrated embodiment, the second actuator 3500 is disposed on (or movably coupled to) the first actuator 3400, which is disposed on or coupled to the proximal end portion 3210 of the housing 3200.

The second actuator 3500 is movable between a first position (illustrated in FIG. 7A) and a second position (illustrated in FIG. 7B) different than the first position. The second actuator 3500 moves the steerable member 3001 in a first direction along the second plane when the second actuator is moved in a first direction (indicated by arrow $A_3$) from its first position to its second position.

The second actuator 3500 is movable in a second direction (indicated by arrow $A_4$ in FIG. 7C) different than its first direction. As the second actuator 3500 is moved (or returned) in its second direction from its second position to its first position, the steerable member 3001 moves in a second direction different than its first direction to or towards its first position.

Figure 7A:
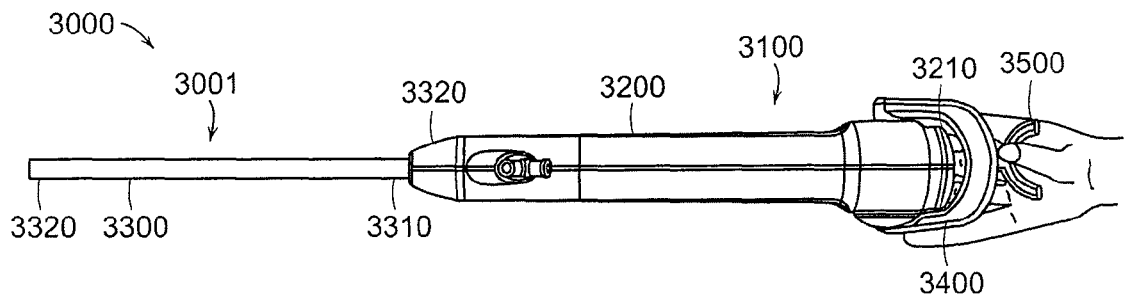
FIGS. 7A-7C are top views of the medical device of FIG. 3 with a second actuator in a first position, second position, and third position, respectively.
Figure 7B:
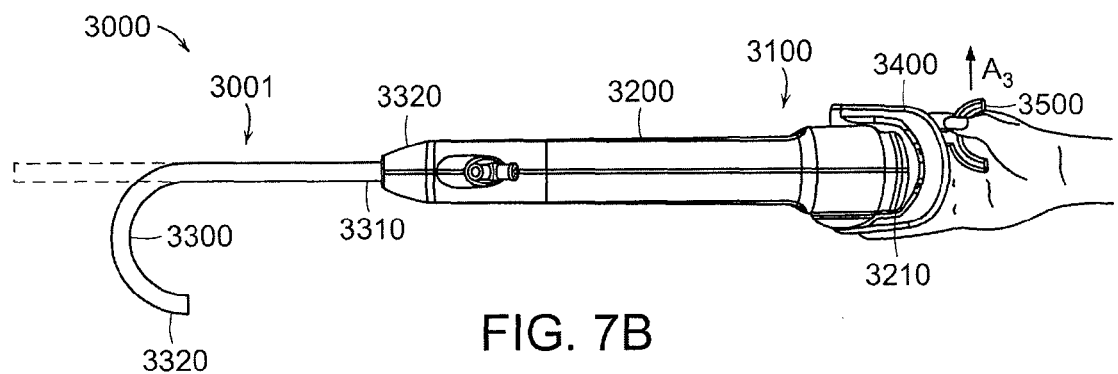
Figure 7C:
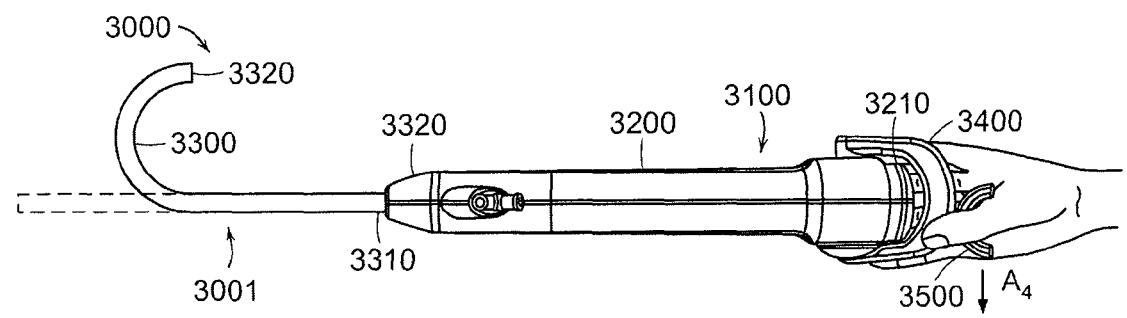

In FIGS. 7B and 7C, the steerable member 3001 is illustrated in an articulated position, with the non-articulated (or relaxed) position of the steerable member illustrated in broken lines. For example, in some embodiments, the steerable member is a catheter or endoscope of greater length (such as compared to the length of the steering mechanism) than the steerable member in the illustrated embodiments.

In some embodiments, the second actuator 3500 is movable to a third position (illustrated in FIG. 7C) different than its first position and its second position. The second actuator 3500 is moved to its third position by moving the second actuator in the second direction different than the first direction, such as from its first or second position to its third position. In some embodiments, for example, the second actuator 3500 is moved in a direction opposite the first direction to move the actuator from at least one of its first or second positions to its third position.

As illustrated in FIG. 6, in some embodiments, the steering mechanism 3100 includes a first horizontal plane wire 3620 and a second horizontal plane wire 3640. Each of the horizontal plane wires 3620, 3640 are movable in response to movement of the second actuator 3500. The first and second horizontal plane wires 3620, 3640 are configured to move the steerable member 3001 of the device 3000 along the second plane different than the first plane, as illustrated in FIGS. 7A-7C.

The first horizontal plane wire 3620 is adapted to move the steerable member in a first direction along the second plane. In some embodiments, the first horizontal plane wire 3620 is coupled to or otherwise engages the second actuator 3500 such that the first horizontal plane wire moves in response to movement of the second actuator.

For example, the first horizontal plane wire 3620 includes a first end and a second end (not shown). In some embodiments, the first end of the first horizontal plane wire 3620 is coupled to (or otherwise engages) the second actuator 3500. The second end of the first horizontal plane wire 3620 is couplable to the steerable member 3001 of the medical device 3000.

As the second actuator 3500 is moved in its first direction, the second actuator moves the first horizontal plane wire 3620, which moves the steerable member 3001 in its first direction, as illustrated in FIG. 7B. In some embodiments, for example, the first horizontal plane wire 3620 is configured to move the steerable member 3001 in a first horizontal direction, such as "right" from the perspective of the user.

The second horizontal plane wire 3640 is adapted to move the steerable member 3001 in a second direction different than the first direction along the second plane, as illustrated in FIG. 7C. In some embodiments, the second horizontal plane wire 3640 is configured to move the steerable member in a second horizontal direction different than the first horizontal direction, such as "left" from the perspective of the user.

The second horizontal plane wire 3640 defines or includes a first end and a second end (not shown). In some embodiments, the first end of the second horizontal plane wire 3640 is coupled to the second actuator 3500. The second end of the second horizontal plane wire 3640 is couplable to the steerable member.

As the second actuator 3500 moves in its second direction, such as towards its third position, the second actuator 3500 moves (or pulls on) the second horizontal plane wire 3640, which moves the steerable member 3001 in its second direction, as illustrated in FIG. 7C.

Thus, the steering mechanism 3100 is adapted to control articulation of the steerable member 3001 along the second plane. Specifically, the second actuator 3500 is adapted to control at least bi-directional movement of the steerable member 3001 along the second plane. For example, in some embodiments, the steerable member is bi-directionally movable along a horizontal plane, such that movement of the second actuator 3500 in its first direction moves at least a portion of the steerable member to the right from the perspective of the user and movement of the second actuator in its second direction moves the at least a portion of the steerable member to the left from the perspective of the user.

In some embodiments, the second actuator 3500 is adapted to directly transfer motion to at least one of the first or second horizontal plane wires 3620, 3640 coupled to a steerable member 3001 of the device. For example, in some embodiments, the second actuator 3500 engages or is coupled to the horizontal plane wire 3620. As the second actuator 3500 is moved from its first position to its second position, the motion generated from the movement of the second actuator transfers directly to the horizontal plane wire 3620, for example, because there is no intermediary structure (like a cam) between the second actuator and the horizontal plane wire.

Although the horizontal and vertical plane wires are described herein as moving the steerable portion along a substantially horizontal or vertical plane, respectively, in other embodiments, the horizontal and/or vertical plane wires can move the steerable portion along a different plane.

As illustrated in FIGS. 3-6, in some embodiments, the second actuator 3500 is a sliding actuator. The second actuator 3500 is moved between its first, second, and third positions by sliding the second actuator in the first and/or second directions (indicated by arrows $A_3$ and $A_4$ in FIGS. 7B & 7C), for example left and right from the perspective of the user. The sliding movement of the second actuator 3500 between its different positions directly transmits the motion onto the horizontal plane wires 3620, 3640 and without any substantial leverage.

Figure 9:
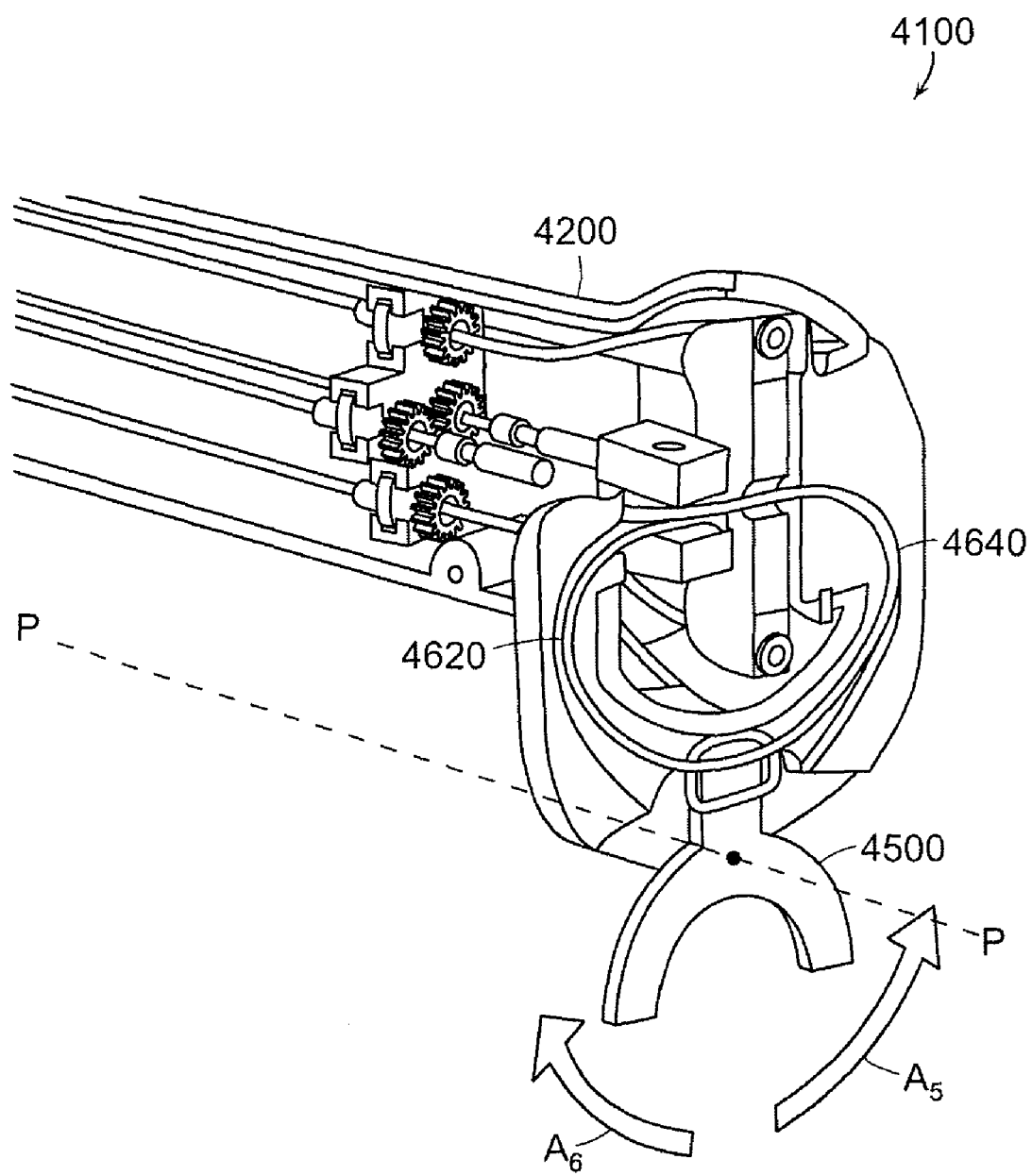
FIG. 9 is a perspective view of a portion of a steering mechanism of a medical device according to an embodiment of the invention.

In other embodiments, the steering mechanism 4100 includes a second actuator 4500 that is a pivoting actuator, as illustrated in FIG. 9. The second actuator 4500 pivots with respect to an axis P. The axis P is parallel to the longitudinal axis L (not illustrated) defined by the housing 4200 of the steering mechanism 4100. As the second actuator 4500 is moved from its first position to its second position in the direction of arrow $A_5$, the second actuator pivots with respect to the axis P. The pivoting movement of the second actuator 4500 introduces motion with force leverage directly onto the horizontal plane wires 4620, 4640. A user can increase the force leverage, for example, by shifting his or her thumb or finger from the middle of the second actuator 4500 to a further edge of the second actuator. The second actuator 4500 is moved (or returned) to its first position from its second position by moving the second actuator in the direction of arrow $A_6$.

Although the second actuator 4500 is illustrated and described as being movable with respect to an axis P that is parallel to the longitudinal axis L defined by the housing 4200, in other embodiments, the axis P is a different axis. For example, in some embodiments, the axis P is coaxial with the longitudinal axis L defined by the housing. In still other embodiments, the axis P is different than, or non-coaxial with, the longitudinal axis L.

The second actuator 3500, 4500 is adapted for at least one-handed operation by a user. In the illustrated embodiment, the second actuator defines a curve or U-shape. The curve or U-shape allows the user to rest a thumb or finger inside the curve or U-shape when manipulating or actuating the second actuator, as illustrated in FIGS. 7A-7C and 8A-8B. For example, during an endoscopic procedure, a physician can hold or rest the housing 4200 of the steering mechanism 4100 in his or her hand and can substantially simultaneously move the second actuator 4500 with the thumb of the same hand. Although the second actuator 4500 is illustrated as a curve or U-shape, the second actuator can be any known shape, for example a circle or a rod.

Furthermore, referring to the embodiment illustrated in FIGS. 3-6, the first actuator 3400 and the second actuator 3500 of the steering mechanism 3100 are adapted for one-fingered operation by a user. For example, during an endoscopic procedure, a physician can move the first actuator 3400 with his or her thumb and, sequentially or substantially simultaneously, move the second actuator 3500 with the same thumb without having to readjust the position of the thumb or hand. For example, one-fingered operation of the steering mechanism 3100 by a user is facilitated when the second actuator 3500 is movably coupled to the first actuator 3400 because the user can maintain the position of his or her hand or finger while moving one or both of the first and second actuators 3400, 3500.

In some embodiments, at least one of the first actuator 3400 and the second actuator 3500 is independently movable of the other of the first actuator and the second actuator. Said another way, the manipulation of one actuator does not affect the position of the other actuator. For example, in one embodiment, the second actuator can be moved between its first position and its second position, and the position of the first actuator is unchanged by movement of the second actuator. In another example, movement of the first actuator from its second position to its third position does not change the position of the second actuator.

In some embodiments, the horizontal plane wires, which direct movement of the steerable member along the second plane, are configured to enter into at least one opening (not shown) spatially located at the pivoting axis of the first actuator, thus permitting movement of one of the horizontal or vertical plane wires without affecting or causing movement of the other of the horizontal or vertical plane wire.

Because the first actuator 3400 and the second actuator 3500 are configured to move the steerable member along the first and second planes, respectively, the steering mechanism 3100 is configured to move the steerable member of the device in substantially any direction 360 degrees around or about the longitudinal axis L. Said another way, the steering mechanism 3100 is adapted to achieve 360 degree articulation of the steerable member.

Although the steering mechanism 3100 has been described above as including a first and a second vertical plane wire 3610, 3630 movable by a first actuator 3400, in other embodiments, the steering mechanism includes a single vertical plane wire. For example, in one embodiment, a steering mechanism includes a vertical plane wire that includes a first end and a second end. The vertical plane wire is couplable to a steerable member of a medical device. For example, in some embodiments, at least one of the first end and the second end of the vertical plane wire is couplable to a first portion of the steerable member.

In some embodiments, each of the first end and the second end of the vertical plane wire is couplable to the steerable member of the device. For example, in some embodiments, the first end of the vertical plane wire is coupled to a first portion of the steerable member, the vertical plane wire extends through a portion of the inner cavity of the housing and around a portion of the cam, and the second end of the vertical plane wire is coupled to a second portion of the steerable member. The portion of the vertical plane wire extending around the cam engages the cam, such as via a groove similar to the groove 3232 described above with respect to FIG. 5.

A portion of the vertical plane wire between the first and second ends of the vertical plane wire is coupled to the first actuator. As the first actuator is moved in a first direction, the vertical plane wire is moved in a first direction, and a steerable member of a medical device is moved in a first direction along a first plane. As the first actuator is moved in a second direction different than the first direction, the vertical plane wire is moved in a second direction, and the steerable member of the medical device is moved in a second direction different than its first direction along the first plane.

Although the steering mechanism 3100 has been described above and illustrated as including a first and a second horizontal plane wire 3620, 3640 movable by a second actuator 3500, in other embodiments, the steering mechanism includes a single horizontal plane wire. For example, in one embodiment, a steering mechanism includes a horizontal plane wire that includes a first end and a second end. The horizontal plane wire is couplable to a steerable member of a medical device. For example, in some embodiments, at least one of the first and the second end of the horizontal plane wire is couplable to a first portion of the steerable member.

In some embodiments, each of the first end and the second end of the horizontal plane wire is couplable to the steerable member of the device. For example, in some embodiments, the first end of the horizontal plane wire is coupled to a first portion of the steerable member, the horizontal plane wire extends through a portion of an inner cavity of a housing, and the second end of the horizontal plane wire is coupled to a second portion of the steerable member.

At least a portion of the horizontal plane wire extending through the inner cavity of the housing is coupled to the second actuator 3500. As the second actuator is moved in a first direction, the horizontal plane wire is moved in a first direction, and a steerable member of a medical device is moved in a first direction along a second plane. As the second actuator is moved in a second direction different than the first direction, the horizontal plane wire is moved in a second direction, and the steerable member of the medical device is moved in a second direction different than its first direction along the second plane.

In some embodiments, as illustrated in FIGS. 3 and 5, the apparatus 3000 includes first and second ports 3270, 3260. The first port 3270 is adapted to be connected to a working channel 3274, or lumen, that extends through at least a portion of the elongated member 3001 of the apparatus 3000 to or towards the distal end 3320 of the elongated member 3001, such as to or towards a treatment site in a body of a patient. The first port 3270 is adapted to receive medical instrumentation. For example, in some embodiments, the first port 3270 is adapted to receive at least one of a guidewire, laser fiber, stone basket, biopsy device, or other medical instrumentation. The first port 3270 allows a physician to insert the medical instrumentation into the working channel 3274, and then through the elongated member 3001 to the treatment site. In one procedure, for example, a portion of a guidewire is passed through the first port 3270, through the working channel 3274, and to the treatment site.

The second port 3260 is adapted to transport an irrigation fluid, such as saline, or gas, such as an air jet, from a source external to the apparatus 3000 into the first port 3270. The second port 3260 is fluidically connected to the first port 3270, which can be fluidically connected to the working channel 3274 extending at least partially through the elongated member 3001. The irrigation fluid can be passed through the second port 3260 to wash the medical instrumentation passed through the first port 3270. In one procedure, for example, an irrigation fluid is passed through the second port 3260 to wash off debris, such as from broken stones being removed from the treatment site by a stone basket that has been passed through the first port 3270.

In the illustrated embodiment, the second port 3260 extends radially from the first port 3270. In some embodiments, the ports 3260, 3270 are configured with a Y-shaped junction, as illustrated in FIG. 5. One or both of ports 3260, 3270 can be monolithically constructed with the housing 3200. In other embodiments, one or both of ports 3260, 3270 can be separately constructed and then disposed on or coupled to the housing 3200. Although ports 3260, 3270 are illustrated as being coupled to the distal end 3220 of the housing 3200, in other embodiments, the ports can be coupled to a different portion of the apparatus 3000.

In some embodiments, the apparatus 3000 includes or is adapted to receive an electrical component (not shown). For example, as illustrated in FIGS. 3 and 5, the apparatus 3000 includes a third port 3250. The third port 3250 is adapted for channeling or receiving at least a portion of the electrical component. For example, in some embodiments, the third port is adapted to receive at least a portion of a signal transmission line. In one procedure, the signal transmission line can extend from a point exterior to the apparatus 3000, through the third port 3250, and through the elongated member 3001 to or towards the distal end 3320 of the elongated member 3001. The signal transmission line, for example, can be adapted to transmit an image received by an optical element at the distal end of the transmission line to an imaging system exterior to the apparatus 3000. In another example, the third port is adapted to receive at least a portion of an electrical component including a fiber optic light and associated electrical cable. In some embodiments, the third port 3250 is monolithically constructed with the housing 3200. In other embodiments, the third port 3250 is separately constructed and then coupled to the housing 3200. Although the third port 3250 is illustrated as being coupled to the distal end 3220 of the housing 3200, in other embodiments, the third port 3250 can be coupled to a different portion of the apparatus 3000.

Although the apparatus 3000 is illustrated and described as including first port 3270, second port 3260, and third port 3250, in other embodiments, the apparatus can include any combination of the first, second, and third ports, only one of the first, second, or third ports, or none.

In a procedure utilizing a steering mechanism according to the present invention, the user can hold or rest the housing in one of the user's hands, or rest the housing on a preferred location. The user places a thumb or finger onto the second actuator. To move the steerable member or portion of the medical device in a vertical direction, the user pulls or otherwise moves the second actuator around the end of the housing. To move the steerable member or portion in a horizontal direction, the user slides, pulls, or otherwise moves the first actuator to the left or to the right from the perspective of the user. The user can substantially simultaneously move both the first actuator and the second actuator to move the steerable member or portion in a direction other than a vertical or horizontal direction. For example, the user can substantially simultaneously move or flip the first actuator around the proximal end portion of the housing and move the second actuator to the right to move the steerable member or portion at a 45 degree angle. The user can also achieve articulation of the steerable member or portion at the 45 degree (or other) angle by sequentially moving the first actuator and the second actuator. The steering mechanism is configured such that the user can control articulation of the steerable member or portion in substantially any angle or direction that is 360 degrees about the longitudinal axis L.

While various embodiments of the invention have been described above, it should be understood that they have been presented by way of example only and are not limiting on the invention. The breadth and scope of the invention should not be limited by any of the above-described embodiments.

The invention claimed is:

1. A steering mechanism for use as part of a medical device, comprising:

a housing including a proximal end portion and a distal end portion, the housing extending along a longitudinal axis, the housing configured to be coupled to a device including a steerable member;

a first actuator movably coupled to the housing, the first actuator configured to move between a first position and a second position different than the first position, the first actuator movable about a first axis different than the longitudinal axis, the first actuator configured to move the steerable member of the device along a first plane when the housing is coupled to the device and when the first actuator is moved between its first position and its second position; and a second actuator coupled to the housing, the second actuator movable between a first position and a second position and movable with respect to a second axis different than the first axis, the second actuator configured to move the steerable member of the device along a second plane different than the first plane when the housing is coupled to the device and when the second actuator is moved between its first position and its second position;

wherein movement of the first actuator results in movement of the second actuator.

2. The steering mechanism of claim 1, wherein the second actuator is independently movable of the first actuator.

3. The steering mechanism of claim 1, wherein the first actuator and the second actuator are adapted for at least one of one-handed or one-fingered operation by a user.

4. The steering mechanism of claim 1, wherein at least one of the first actuator and the second actuator is adapted to introduce force leverage to a portion of the steering mechanism when the at least one of the first actuator and the second actuator is moved by a user.

5. The steering mechanism of claim 1, wherein the first actuator is adapted to move the steerable member of the device along a substantially vertical plane.

6. The steering mechanism of claim 1, wherein the second actuator is adapted to move the steerable member of the device along a substantially horizontal plane.

7. The steering mechanism of claim 1, the housing further comprising:
 a cam disposed in the housing, the cam coupled to the first actuator, the cam movable between a first position and a second position different than the first position.

8. The steering mechanism of claim 7, further comprising:
 a wire including a first end and a second end, at least a portion of the wire engaged with the cam, at least a portion of the wire couplable to the steerable member of the device.

9. The steering mechanism of claim 1, wherein the second actuator is adapted to directly transfer motion to a wire coupled to the steerable member of the device.

10. The steering mechanism of claim 1, wherein the second actuator is movably coupled to the first actuator.

11. The steering mechanism of claim 1, wherein the first actuator and the second actuator are disposed on the proximal end portion of the housing.

12. The steering mechanism of claim 1, wherein the first actuator is movable with respect to an axis that is orthogonal to the longitudinal axis defined by the housing.

13. A medical device, comprising:
 an elongated member including a proximal end and a distal end and defining a lumen at least partially therethrough, the elongated member substantially extending along a longitudinal axis, the elongated member including a steerable portion, at least a portion of the steerable portion being movable along a first plane and a second plane different than the first plane such that the steerable portion of the elongated member is movable in substantially any direction 360 degrees around the longitudinal axis; and
 a steering mechanism couplable to the elongated member, the steering mechanism adapted for one-fingered operation by a user, the steering mechanism configured to move the steerable portion of the elongated member along the first plane and along the second plane different than the first plane, the steering mechanism comprising:
  a first actuator movable about a first axis different than the longitudinal axis, the first actuator adapted to move the steerable portion of the elongated member along the first plane; and
  a second actuator adapted to move the steerable portion of the elongated member along the second plane, the second actuator selectively actuatable substantially simultaneously with the first actuator;
 wherein movement of the first actuator results in movement of the second actuator.

14. The medical device of claim 13, wherein the steering mechanism includes a housing, the housing defining a proximal end portion and a distal end portion, the elongated member couplable to the distal end portion of the housing of the steering mechanism.

15. The medical device of claim 13, wherein the second actuator is movably coupled to the first actuator.

16. The medical device of claim 13, further comprising:
 a first horizontal plane wire coupled to the steerable portion of the elongated member, at least a portion of the first horizontal plane wire coupled to the second actuator, the first horizontal plane wire movable in response to movement of the second actuator, the first horizontal plane wire adapted to move the steerable portion of the elongated member in a first direction along the second plane; and
 a second horizontal plane wire coupled to the steerable portion of the elongated member, at least a portion of the second horizontal plane wire coupled to the second actuator, the second horizontal plane wire movable in response to movement of the second actuator, the second horizontal plane wire adapted to move the steerable portion of the elongated member in a second direction along the second plane different than the first direction along the second plane.

17. The medical device of claim 13, further comprising:
 a vertical plane wire, wherein a first portion of the vertical plane wire is coupled to the first actuator and a second portion of the vertical plane wire is coupled to the steerable portion of the elongated member; and
 a horizontal plane wire, wherein a first portion of the horizontal plane wire is coupled to the second actuator and a second portion of the horizontal plane wire is coupled to the steerable portion of the elongated member.

18. The medical device of claim 17, wherein the housing of the steering mechanism defines an interior cavity, the vertical plane wire and the horizontal plane wire each extending from the steerable portion of the elongated member through at least a portion of the interior cavity of the housing.

19. The medical device of claim 13, the steering mechanism further comprising:
 a housing defining an interior cavity; and
 a cam disposed in the interior cavity defined by the housing, the cam coupled to the first actuator and configured to move between a first position and a second position different than the first position in response to movement of the first actuator.

20. The medical device of claim 19, further comprising:
 a first vertical plane wire coupled to the steerable portion of the elongated member, at least a portion of the first vertical plane wire coupled to the cam, the first vertical plane wire movable in response to movement of the first actuator, the first vertical plane wire adapted to move the steerable portion of the elongated member in a first direction along the first plane; and
 a second vertical plane wire coupled to the steerable portion of the elongated member, at least a portion of the second vertical plane wire coupled to the cam, the second vertical plane wire movable in response to movement of the first actuator, the second vertical plane wire adapted to move the steerable portion of the elongated member in a second direction along the first plane different than the first direction along the first plane.

* * * * *